(12) United States Patent
Ramorino et al.

(10) Patent No.: US 11,986,172 B2
(45) Date of Patent: May 21, 2024

(54) DEVICE FOR COLLECTING SAMPLES OF BIOLOGICAL TISSUE

(71) Applicant: Euromedical S.R.L., San Zeno Naviglio (IT)

(72) Inventors: Giorgio Ramorino, San Zeno Naviglio (IT); Ilario Bonera, Brescia (IT)

(73) Assignee: EUROMEDICAL S.R.L., San Zeno Naviglio (IT)

( * ) Notice: Subject to any disclaimer, the term of this patent is extended or adjusted under 35 U.S.C. 154(b) by 741 days.

(21) Appl. No.: 17/255,180

(22) PCT Filed: Jun. 27, 2019

(86) PCT No.: PCT/IB2019/055456
§ 371 (c)(1),
(2) Date: Dec. 22, 2020

(87) PCT Pub. No.: WO2020/003198
PCT Pub. Date: Jan. 2, 2020

(65) Prior Publication Data
US 2021/0244391 A1  Aug. 12, 2021

(30) Foreign Application Priority Data
Jun. 27, 2018  (IT) ......................... 102018000006731

(51) Int. Cl.
*A61B 10/04*  (2006.01)
*A61B 1/005*  (2006.01)
(Continued)

(52) U.S. Cl.
CPC ............. *A61B 10/04* (2013.01); *A61B 1/005* (2013.01); *A61B 1/018* (2013.01);
(Continued)

(58) Field of Classification Search
None
See application file for complete search history.

(56) References Cited

U.S. PATENT DOCUMENTS

| 6,106,484 A | 8/2000 | Terwilliger |
| 2004/0068231 A1* | 4/2004 | Blondeau ........... A61B 10/0275 604/157 |

(Continued)

FOREIGN PATENT DOCUMENTS

WO  WO2014/061505  4/2014

OTHER PUBLICATIONS

International Search Report and Written Opinion of the International Searching Authority dated Oct. 21, 2019, in connection with International Application No. PCT/IB2019/055456 (14 pages).

*Primary Examiner* — Jay B Shah
(74) *Attorney, Agent, or Firm* — Kllintworth & Rozenblat IP LLP

(57) ABSTRACT

A device (1) for collecting samples of biological tissue, comprising a needle (3) and a cannula (4), positioned at a distal end (5) of the device (1) and coaxially arranged along an axis (A) and slidable with respect to each other along the axis (A); a covering sheath (6), surrounding the needle (3) and the cannula (4); and an actuating mechanism (7), positioned at a proximal end (8) of the device (1) and connected to the needle (3) and the cannula (4) for moving the needle (3) and the cannula (4) in the sheath (6); wherein the actuating mechanism (7) is connected to the needle (3) and the cannula (4) by respective flexible operation cables (10a, 10b), capable of transmitting axial forces in both directions.

15 Claims, 7 Drawing Sheets

(51) Int. Cl.
  *A61B 1/018* (2006.01)
  *A61B 10/02* (2006.01)
(52) U.S. Cl.
  CPC .. *A61B 10/0233* (2013.01); *A61B 2010/0208* (2013.01); *A61B 2010/045* (2013.01)

(56) References Cited

U.S. PATENT DOCUMENTS

| | | |
|---|---|---|
| 2012/0022397 A1 | 1/2012 | Jarial |
| 2014/0088456 A1 | 3/2014 | Wang |
| 2017/0340352 A1 | 11/2017 | Stone et al. |
| 2018/0249894 A1* | 9/2018 | Kolberg ............ A61B 1/00137 |

* cited by examiner

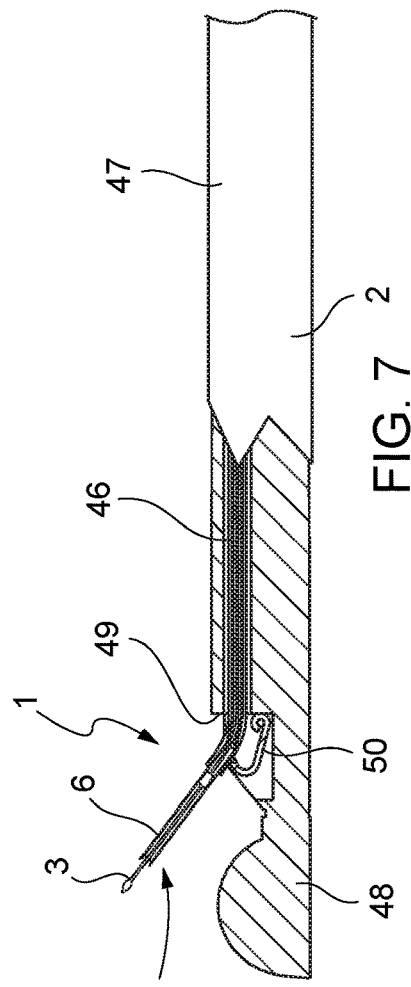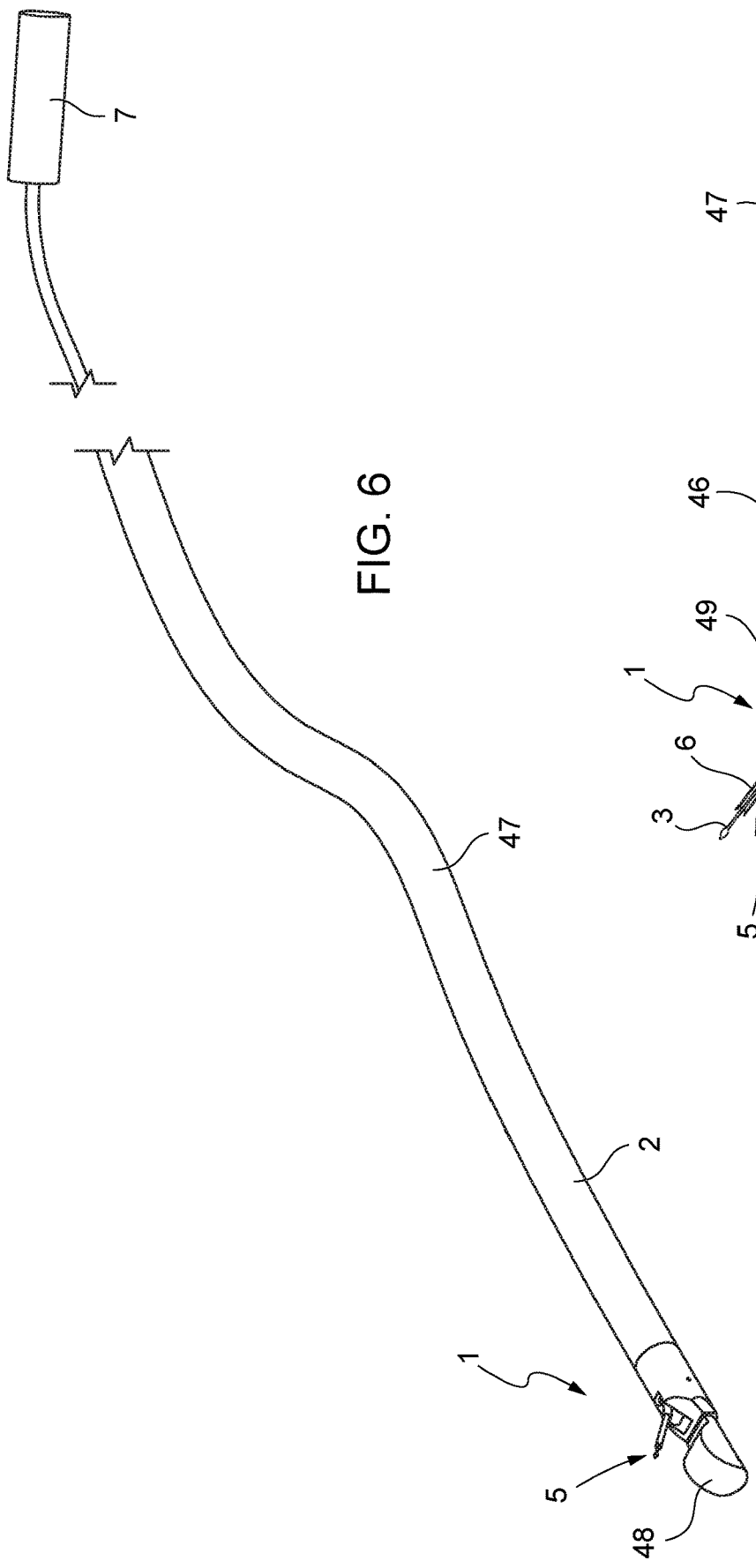

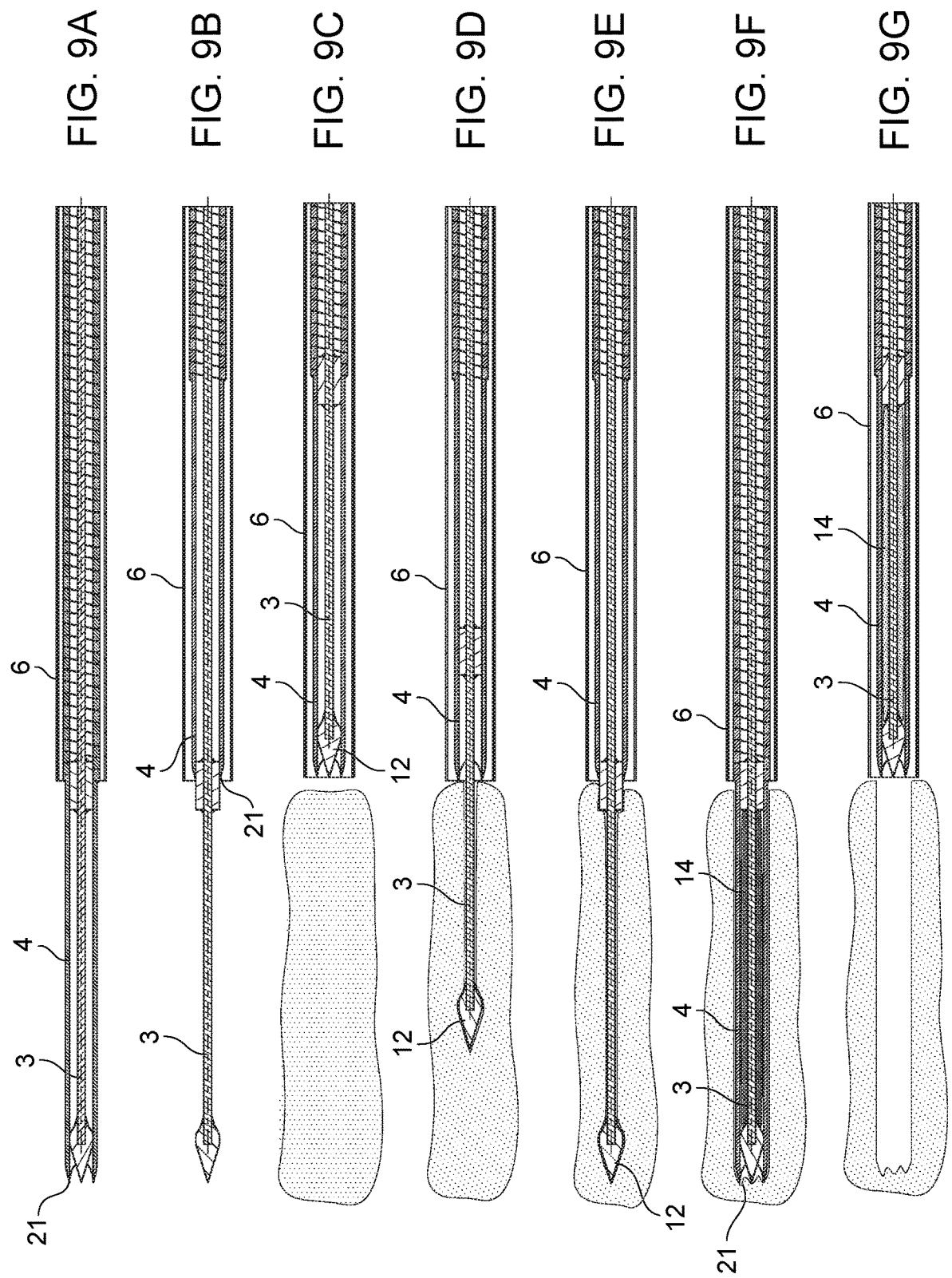

DEVICE FOR COLLECTING SAMPLES OF BIOLOGICAL TISSUE

CROSS-REFERENCE TO RELATED APPLICATIONS

This patent application claims priority from Italian patent application no. 102018000006731 filed on Jun. 27, 2018, the entire disclosure of which is incorporated herein by reference.

TECHNICAL FIELD

The present invention concerns a device for collecting samples of biological tissue.

BACKGROUND ART

In the medical-diagnostic field, the need to collect samples of biological tissue is known, also from internal organs, in order to carry out subsequent tests on them.

Different types of devices for collecting samples of biological tissue are known. In general, these devices comprise a collecting needle, movable from a non-operating position to an operating position to penetrate into the tissue to be examined, and vice versa.

However, the known devices appear to have room for improvement, in particular in terms of effectiveness, operating reliability and simplicity of construction.

In particular, a problem often encountered in the known devices is the rigidity of the needle, which makes it difficult to use in conjunction with an endoscope when operating along particularly winding paths or in the presence of obstacles or impediments.

Furthermore, the known devices do not always ensure the collection of samples suitable for subsequent analysis, and therefore it is often necessary to repeat the collection to obtain a suitable sample.

DISCLOSURE OF INVENTION

An object of the present invention is to provide a device for collecting samples of biological tissue that overcomes the drawbacks of the known art.

In particular, an object of the invention is to provide a collection device which is extremely effective and reliable.

The present invention therefore concerns a device for collecting samples of biological tissue as defined in the attached claim 1 and, for the additional characteristics, as defined in the dependent claims.

The device of the invention for collecting samples of biological tissue is simple to produce and use and fully effective and reliable in the collecting function, being furthermore fully suitable, also due to the flexibility of its end part designed for collecting the samples, for use in conjunction with an endoscope, also within the operating channel of the endoscope.

BRIEF DESCRIPTION OF THE DRAWINGS

Further characteristics and advantages of the present invention will become clear from the description of the following non-limiting embodiment examples, with reference to the figures of the attached drawings, in which:

FIG. 6 is a partial perspective schematic view of an endoscope provided with the device of FIG. 1;

FIG. 7 is a schematic view in longitudinal section of a detail of the endoscope of FIG. 6;

FIGS. 9A-9G show schematically the operation of the device of the invention.

BEST MODE FOR CARRYING OUT THE INVENTION

Figure 1:
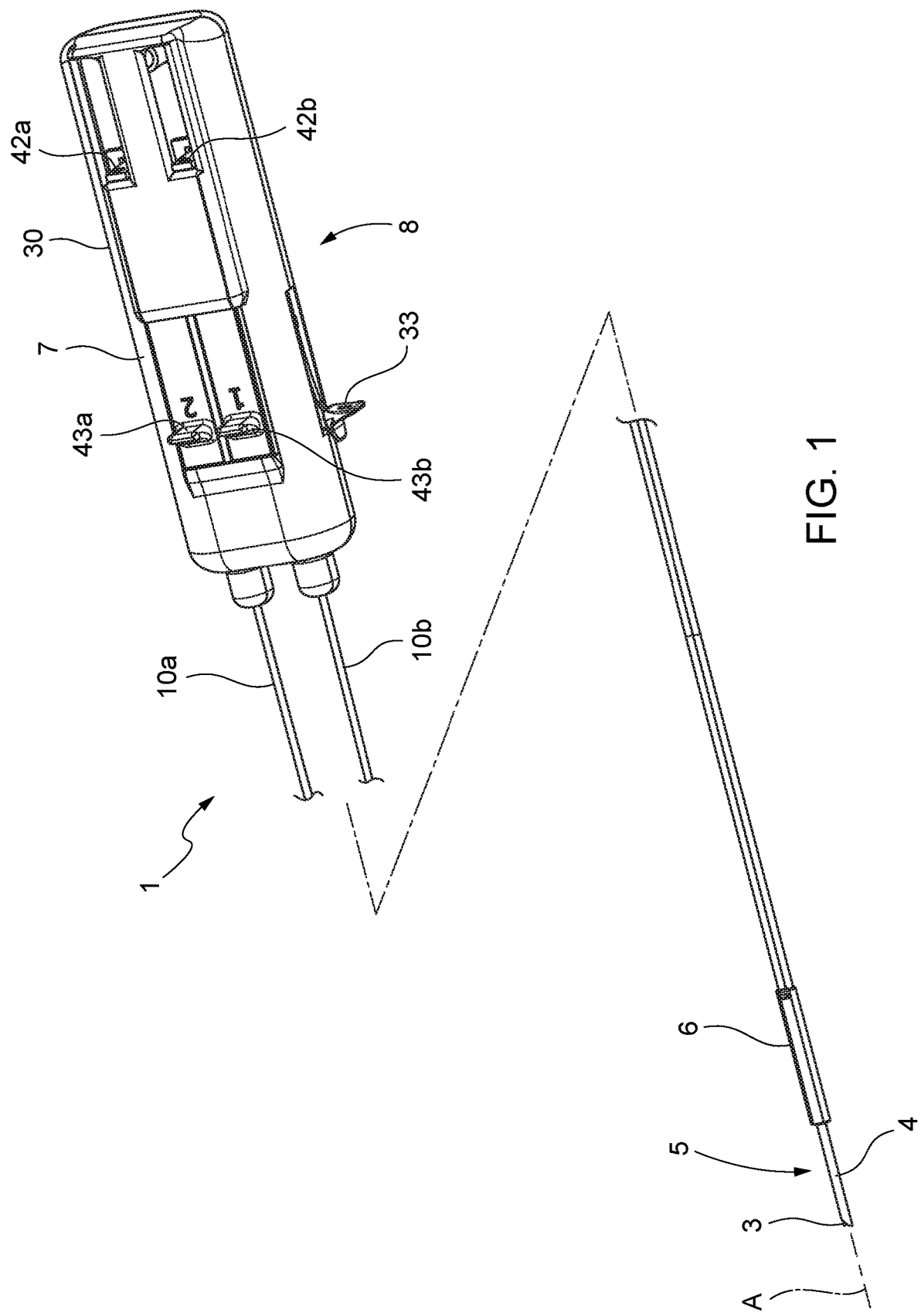
FIG. 1 is a perspective schematic view of a device for collecting biological samples in accordance with the invention.

In FIG. 1 the number 1 indicates overall a device for collecting samples of biological tissue, in particular for collecting tissue samples of internal organs of a human or animal body, comprising a needle 3 and a cannula 4, arranged coaxial along an axis A at a distal end 5 of the device 1 and cooperating to collect a tissue sample; a covering sheath 6, which surrounds the needle 3 and the cannula 4; and an actuating mechanism 7, positioned at a proximal end 8 of the device 1 and connected to the needle 3 and to the cannula 4 by means of respective operation cables 10a, 10b to move the needle 3 and the cannula 4 in the sheath 6.

Figure 2:
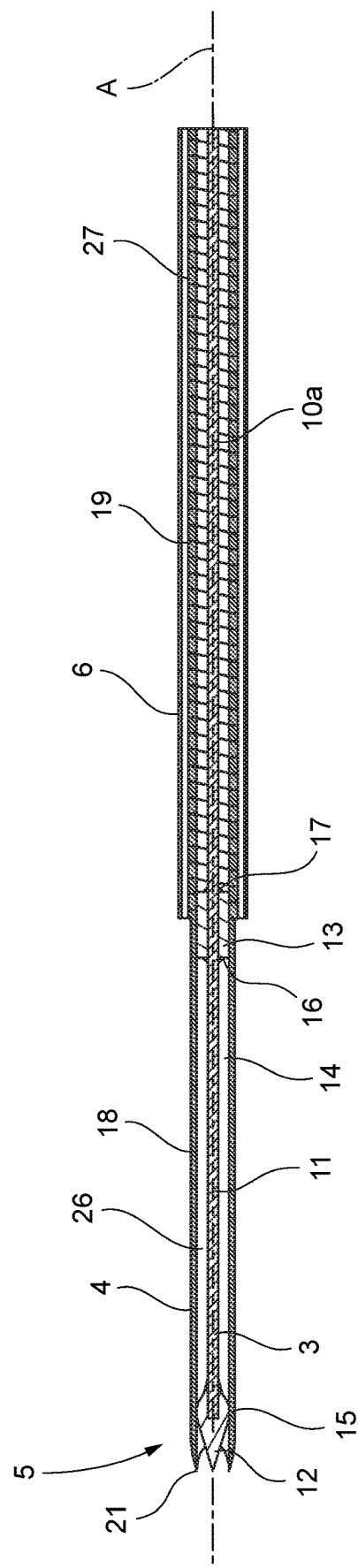
FIG. 2 is a longitudinal section view of a detail of the device of FIG. 1, in particular of a distal end thereof provided with a needle and a cannula cooperating in collection of the samples.
Figure 3:
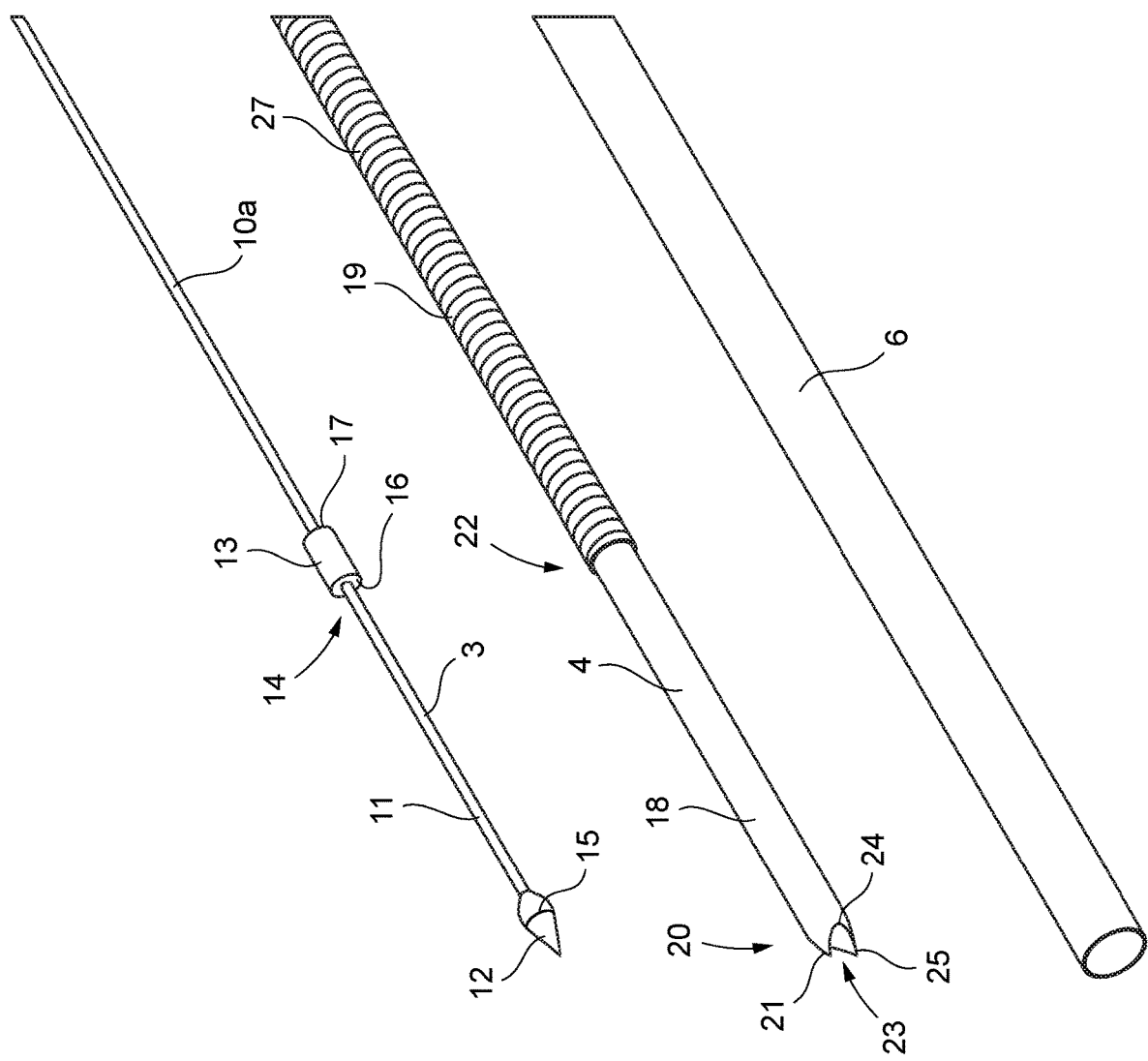
FIGS. 3A, 3B, 3C are perspective views of respective components of the device of FIG. 1.

With reference also to FIGS. 2 and 3A, the needle 3, made of metallic material for example, extends along the axis A and has a cylindrical stem 11 provided with a front tip 12 and a rear end element 13, positioned at respective axially opposite ends of the stem 11 and delimiting a collecting seat 14 shaped to receive a tissue sample.

The tip 12 and the end element 13 radially protrude from the stem 11 and extend radially about the axis A and have a substantially circular cross section.

Preferably, the tip 12 and the end element 13 have a maximum diameter equal to each other.

The tip 12 and the end element 13 axially delimit the seat 14, which is positioned on the stem 11 between the tip 12 and the end element 13.

Advantageously, the seat 14 extends all around the stem 11 and therefore the axis A and is symmetrical about the axis A.

The tip 12 preferably has a double cone shape, having a front conical portion and an opposite rear truncated-cone portion, joined to each other in a maximum diameter section 15 of the tip 12.

The end element 13 is provided with a front wall 16, which projects from the stem 11 and faces towards the tip 12 and delimits at the rear the seat 14, and a rear wall 17, opposite the front wall 16 and facing towards the actuating mechanism 7; in the embodiment example illustrated, the wall 16 is substantially annular around the stem 11 and substantially perpendicular to the axis A. The wall 16 has an external diameter substantially equal to the maximum diameter of the tip 12 (diameter of the section 15).

The end element 13 is, for example, substantially cylindrical.

The needle 3 is joined, in particular by means of the end element 13, to the cable 10a connected to the actuating mechanism 7.

The cable 10a is a flexible cable, for example metallic, capable of transmitting axial forces in both directions.

In the example illustrated, the cable 10a is fixed (for example, welded) centrally to the rear wall 17 of the end element 13 and is axially aligned with the stem 11.

Optionally, the position of the end element 13 on the stem 11 is axially adjustable, for example by means of a threaded coupling or other equivalent system, so as to vary the distance of the end element 13, in particular of the wall 16, from the tip 12 and therefore also vary the axial length of the seat 14.

With specific reference to FIGS. 2 and 3B, the cannula 4 is substantially tubular and internally hollow and extends along the axis A around the needle 3, radially external relative to the needle 3.

The cannula 4 comprises an operating portion 18, cooperating with the needle 3 to collect the sample, and optionally a flexible connection portion 19, joined to the operating portion 18 and positioned around the cable 10a.

The operating portion 18 extends axially between a free end 20, having a cutting edge 21; and a root end 22, opposite the free end 20 and joined to the connection portion 19.

In further detail, the free end 20 has a front opening 23 delimited by a peripheral rim 24 defining the cutting edge 21; the rim 24 is shaped to form at least an axially protruding tip 25; in the preferred embodiment shown, the cutting edge 21 is double-pointed and the rim 24 has a pair of diametrically opposite points 25, joined by two saddle-shaped rim portions.

The operating portion 18 is hollow inside and is provided with an inner chamber 26 substantially cylindrical about the axis A, communicating with the opening 23. The chamber 26 and the opening 23 have an internal diameter substantially equal to the maximum diameter of the tip 12 (and of the end element 13).

The connection portion 19 is for example defined by a flexible pipe 27, for example a spiral pipe or a pipe with interconnected annular sectors.

In a variation, the operating portion 18 of the cannula 4 consists of an end portion of the same pipe 27, for example spiral or with interconnected annular sectors, defining the connection portion 19.

The operating portion of the cannula 4 is operated by means of the cable 10b connected to the actuating mechanism 7. Also the cable 10b is a flexible cable, for example metallic, capable of transmitting axial forces in both directions.

With specific reference to FIGS. 2 and 3C, the sheath 6 is radially positioned on the outside of the cannula 4 and around the cannula 4 along the axis A.

The sheath 6 is a flexible tubular sheath, for example made of polymeric material.

In accordance with the invention, also the needle 3 and the cannula 4 are at least partially substantially flexible.

In one embodiment, the stem 11 of the needle 3 has dimensions (diameter and possibly length) such as to be substantially flexible crosswise, even if made of metallic material.

Analogously, also the operating portion 18 of the cannula 4 has dimensions (in particular, wall diameter and thickness) such as to be substantially flexible crosswise.

In this way, the entire assembly formed of the needle 3, the cannula 4, the respective cables 10a, 10b and the sheath 6 is flexible.

In other embodiments, the operating portion 18 of the cannula 4 and the needle 3 have a sufficiently short length to be able to follow relatively winding paths even if the operating portion 18 and the needle 3 are substantially rigid.

The needle 3 and the cannula 4 are actuated by means of the actuating mechanism 7 acting on the cables 10a, 10b.

The actuating mechanism 7 can be of different types.

Figure 4:
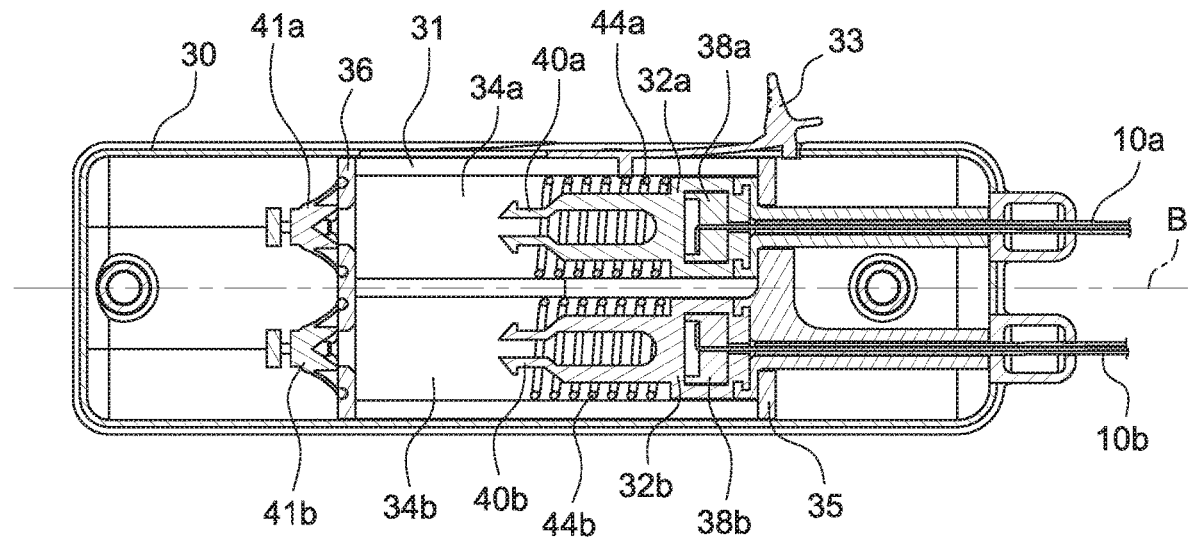
FIGS. 4 and 5 are two section views according to respective orthogonal planes of a further detail of the device of FIG. 1, in particular of a proximal end thereof provided with an actuating mechanism.
Figure 5:
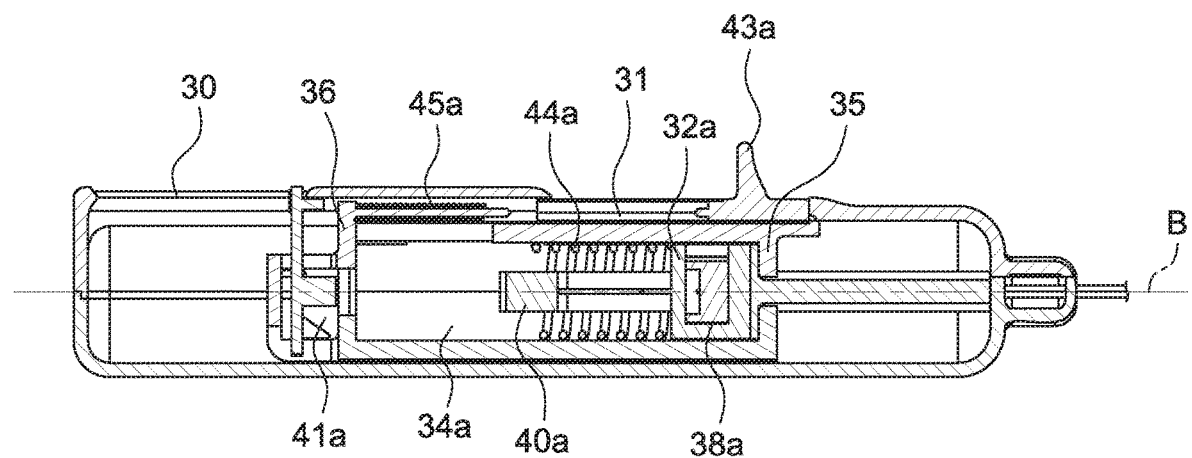

In the preferred embodiment shown in FIG. 1 and in further detail in FIGS. 4-5, the actuating mechanism 7 comprises a casing 30 which houses a slide 31 in which a pair of carriages 32a, 32b are positioned side-by-side.

The slide 31 is housed and slides along an axis B in the casing 30 and is connected to a recovery button 33 protruding from the casing 30.

The slide 31 has a pair of guides 34a, 34b parallel to the axis B axially delimited by a front wall 35 and a rear wall 36 of the slide 31.

The carriages 32a, 32b are housed axially slidable in respective guides 34a, 34b and are connected to the cables 10a, 10b respectively to actuate the needle 3 and the cannula 4.

In particular, the carriages 32a, 32b extend along respective longitudinal axes parallel to each other and to the axis B between respective first ends provided with respective heads 38a, 38b fixed to an end of a cable 10a, 10b (arranged passing through a through opening in the front wall 35), and respective second ends provided with respective releasable coupling members 40a, 40b which engage respective triggers 41a, 41b connected to respective shooting buttons 42a, 42b protruding from the casing 30.

The carriages 32a, 32b are connected to respective loading buttons 43a, 43b, which project laterally from the respective carriages 32a, 32b to the outside of the casing 30.

Each carriage 32a, 32b comprises a respective main spring 44a, 44b which extends around the carriage 32a, 32b from the head 38a, 38b towards the rear wall 36; and a return spring 45a, 45b (only one of which can be seen in FIG. 5), acting on the respective loading button 43a, 43b and interposed between the loading button 43a, 43b and the rear wall 36.

The device 1 is advantageously used in conjunction with an endoscope 2, as shown by way of example in the preferred embodiment of FIGS. 6-7.

The device 1 is configured so as to be housed (at least partly) inside an operating channel of the endoscope 2, which can be any traditional endoscope.

In particular, the device 1 is configured so that the sheath 6 containing the needle 3 and the cannula 4 can be inserted inside an operating channel 46 of the endoscope 2; it is understood that the device 1 can be used also externally to the channel 46 of the endoscope 2.

The endoscope 2 comprises a flexible tubular body 47 which extends between a head 48 and a handgrip (not illustrated), positioned at respective opposite ends of the body 47.

The channel 46 is arranged along the body 47 inside the body 47 and ends with an opening 49 in the head 48.

The head 48 is provided with an orientation mechanism 50, adjacent to the opening 49, for example a so-called Albarran lever, which can be operated from the handgrip of the endoscope 2 (in a known manner) and cooperating with the distal end 5 of the device 1 to orient the needle 3.

Expediently, the actuating device 7 is positioned on the handgrip of the endoscope 2.

Figure 8:
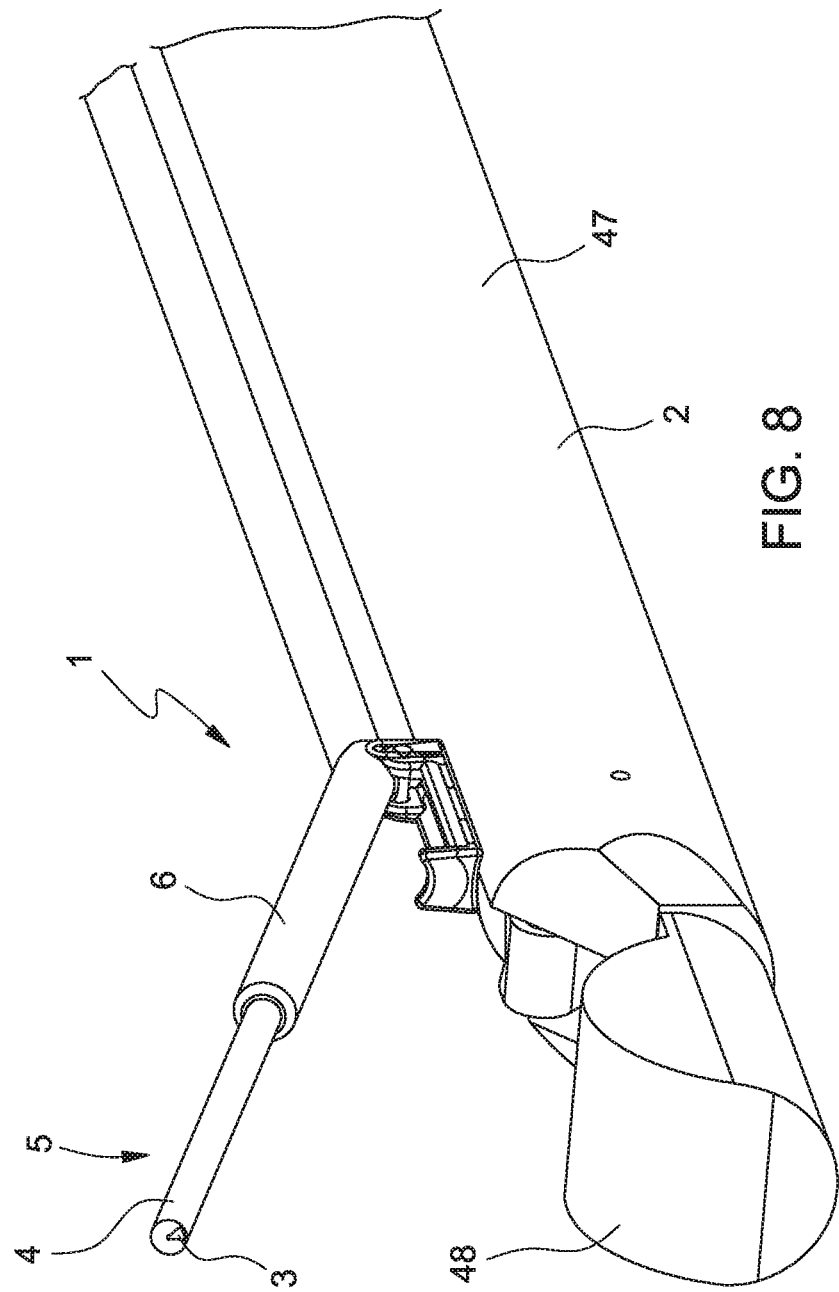
FIG. 8 is a partial perspective schematic view of a further endoscope provided with the device of the invention.

In the variation of FIG. 8, the device 1 is positioned on the outside of the endoscope 2. In particular, the sheath 6 which houses the needle 3 and the cannula 4 of the device 1 is arranged adjacent to the body 47 along the body 47 of the endoscope 2 and is supported laterally by the body 47.

With reference also to FIGS. 9A-9G, operation of the device 2 is as follows.

At rest, i.e. when the device 1 is unloaded, the needle 3 and the cannula 4 are in respective extracted positions relative to the sheath 6 and protrude to the outside of the sheath 6 (FIG. 9A). The needle 3 is entirely surrounded by the cannula 4.

Firstly the operator loads the cannula 4, acting on the respective loading button 43b connected to the cannula 4 by means of the cable 10b. In particular, the operator moves the carriage 32b in the guide 34b by compressing the spring 44b against the wall 36 and causing the releasable coupling member 40b to engage the trigger 41b. The cannula 4 retracts with respect to the needle 3 and the sheath 6 and assumes a retracted position (FIG. 9B) in which it is entirely housed inside the sheath 6 (namely the cutting edge 21 does not protrude from the sheath 6).

The operator then loads the needle 3, acting on the respective loading button 43a connected to the needle 3 by means of the cable 10a. In particular, the operator moves the carriage 32a in the guide 34a by compressing the spring 44a against the wall 36 and causing the releasable coupling member 40a to engage the trigger 41a. The needle 3 retracts with respect to the cannula 4 and the sheath 6 and assumes a retracted position (FIG. 9C) in which it is entirely housed within the sheath 6 (namely, the tip 12 does not protrude from the sheath 6).

At this point the device 1 is loaded and the operator can introduce the device 1 into the endoscope 2, in particular inserting the sheath 6 into the channel 46 of the endoscope 2.

The operator then operates the endoscope 2 to bring the device 1 into the organ to be analysed and positions the distal end 5 of the device 1 in the correct collection direction with the help of the orientation mechanism 50 (Albarran lever) of the endoscope 2, if necessary.

At this point the operator releases the needle 3, by pressing the corresponding shooting button 42a which releases the releasable coupling member 40a: the spring 44a moves the carriage 32a and consequently, by means of the cable 10a, the needle 3 which comes out of the cannula 4 and the sheath 6 and assumes the extracted position (FIGS. 9D-9E), penetrating into the tissue from which the sample is to be collected. The penetration depth of the needle 3 can optionally be adjusted by the operator.

Subsequently, the operator also releases the cannula 4, by pressing the corresponding shooting button 42b which releases the releasable coupling member 40b: the spring 44b moves the carriage 32b and consequently, by means of the cable 10b, the cannula 4 which comes out of the sheath 6 and sets to the extracted position (FIG. 9F) to cover the needle 3, cutting with the cutting edge 21 the sample that remains in the seat 14.

The needle 3 and the cannula 4 are then re-set together to the retracted position (FIG. 9G), by acting on the recovery button 33 which moves the slide 31 and drags with it both the carriages 32a, 32b.

The device 1 can now be extracted, together with the endoscope 2 or separately, to remove the sample from the seat 14.

Optionally, it is possible to remove only the needle 3 and the cannula 4, leaving the sheath 6 (and the endoscope 2) in position, so that other samples can be collected.

Lastly, it is understood that modifications and variations that do not depart from the scope of the attached claims can be made to the device described and illustrated here.

The invention claimed is:

1. A device (1) for collecting samples of biological tissue, comprising a needle (3) and a cannula (4), positioned at a distal end (5) of the device (1) and coaxially arranged along an axis (A) and slidable with respect to each other along the axis (A); a covering sheath (6), surrounding the needle (3) and the cannula (4); and an actuating mechanism (7), positioned at a proximal end (8) of the device (1) and connected to the needle (3) and the cannula (4) for moving the needle (3) and the cannula (4) in the sheath (6); wherein the actuating mechanism (7) is connected to the needle (3) and the cannula (4) by respective flexible operation cables (10a, 10b), capable of transmitting axial forces in both directions;

wherein the needle (3) has a stem (11) provided with a front tip (12) and a rear end element (13), positioned at respective axially opposite ends of the stem (11) and radially protruding from the stem (11) and extending radially about the stem (11) to define a collecting seat (14) shaped to receive a sample of tissue, and the position of the end element (13) on the stem (11) is adjustable axially to change the distance of the end element (13) from the tip (12) and thus the axial length of the seat (14).

2. A device according to claim 1, wherein the needle (3) and the cannula (4) have respective portions that are flexible.

3. A device according to claim 1, wherein the seat (14) extends all around the stem (11) and the axis (A) and is symmetrical about the axis (A).

4. A device according to claim 1, wherein the tip (12) and the end element (13) have maximum diameters that are equal to each other.

5. A device according to claim 1, wherein the tip (12) has a double-cone shape, and further having a front conical portion and an opposite rear truncated-cone portion that are joined to each other in a maximum diameter section (15) of the tip (12).

6. A device according to claim 1, wherein the needle (3) and the cannula (4) are movable independently from each other between respective extracted positions, in which the needle (3) and the cannula (4) project outside the sheath (6); and respective retracted positions, in which the needle (3) and cannula (4) are completely housed inside the sheath (6).

7. A device according to claim 6, wherein the actuating mechanism (7) is configured to move the needle (3) and the cannula (4) from the extracted positions to the respective retracted positions and vice versa by the respective cables (10a, 10b).

8. A device according to claim 1, wherein the actuating mechanism (7) comprises a casing that houses a slide (31) slidable along a first axis (B) in the casing (30); and a pair of carriages (32) arranged side-by-side, axially slidable in respective guides (34a, 34b) formed parallel to the first axis (B) on the slide (31), the carriages (32) being connected, by the respective cables (10a, 10b), to the needle (3) and the cannula (4) respectively.

9. An endoscope (2) comprising a flexible tubular body (47) and a head (48), positioned at an end of the body (47) and having a channel (46) arranged along the body (47) inside the body (47) and ending with an opening (49) in the head (48); characterized by comprising a device (1) for collecting samples of biological tissue according to claim 1.

10. An endoscope according to claim 9, wherein the sheath (6) which houses the needle (3) and the cannula (4)

of the device (1) is positioned in the channel (46) of the endoscope (2), or is supported adjacent to the endoscope (2) and side-by-side with the channel (46).

11. An endoscope according to claim 10, wherein the head (48) is provided with an orientation mechanism (50) adjacent to the opening (49) and cooperating with a distal end (5) of the device (1) to orient the needle (3) of the device (1).

12. A device for collecting samples of biological tissue, comprising a needle (3) and a cannula (4), positioned at a distal end (5) of the device (1) and coaxially arranged along an axis (A) and slidable with respect to each other along the axis (A); a covering sheath (6), surrounding the needle (3) and the cannula (4); and an actuating mechanism (7), positioned at a proximal end (8) of the device (1) and connected to the needle (3) and the cannula (4) for moving the needle (3) and the cannula (4) in the sheath (6); wherein the actuating mechanism (7) is connected to the needle (3) and the cannula (4) by respective flexible operation cables (10a, 10b), capable of transmitting axial forces in both directions;

wherein the needle (3) has a stem (11) provided with a front tip (12) and a rear end element (13), positioned at respective axially opposite ends of the stem (11) and radially protruding from the stem (11) and extending radially about the stem (11) to define a collecting seat (14) shaped to receive a sample of tissue; and wherein the cannula (4) comprises an operating portion (18) cooperating with the needle (3) to collect the sample and provided, at a free end (20), with a front opening (23) delimited by a peripheral rim (24) defining a cutting edge (21) and with an inner chamber (26) substantially cylindrical about the axis (A), communicating with the front opening (23) and having an inner diameter substantially equal to the maximum diameter of the tip (12).

13. A device according to claim 12, wherein the cutting edge (21) is double-pointed and the rim (24) has a pair of diametrically opposite points (25), joined by two saddle-shaped rim portions.

14. A device according to claim 12, wherein the cannula (4) comprises a flexible connection portion (19), joined to the operating portion (18) provided with the cutting edge (21) and defined by a flexible pipe (27).

15. A device according to claim 12, wherein the stem (11) of the needle (3) and the operating portion (18) of the cannula (4) have dimensions such as to be substantially flexible crosswise to the axis (A).

* * * * *